(12) United States Patent
Veilleux et al.

(10) Patent No.: US 11,337,760 B2
(45) Date of Patent: May 24, 2022

(54) AUTOMATED HIP ANALYSIS METHODS AND DEVICES

(71) Applicant: Virginia Commonwealth University, Richmond, VA (US)

(72) Inventors: Nathan J. Veilleux, Richmond, VA (US); Jennifer S. Wayne, Chesterfield, VA (US); Niraj V. Kalore, Midlothian, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 17 days.

(21) Appl. No.: 16/365,813

(22) Filed: Mar. 27, 2019

(65) Prior Publication Data

US 2019/0298452 A1 Oct. 3, 2019

Related U.S. Application Data

(60) Provisional application No. 62/648,602, filed on Mar. 27, 2018.

(51) Int. Cl.
*A61B 34/10* (2016.01)
*A61F 2/36* (2006.01)
(Continued)

(52) U.S. Cl.
CPC ............ *A61B 34/10* (2016.02); *A61F 2/3609* (2013.01); *A61B 2034/102* (2016.02);
(Continued)

(58) Field of Classification Search
CPC .......... A61F 2/32; A61F 2/3609; A61B 34/10; A61B 2034/102; A61B 2034/105;
(Continued)

(56) References Cited

U.S. PATENT DOCUMENTS 10,736,539 B2 * 8/2020 Mahfouz .............. A61B 6/5235
2011/0243416 A1 * 10/2011 Gregory ................ G06T 7/0014
382/131

(Continued)

OTHER PUBLICATIONS

Tan et al. "Acetabular rim and surface segmentation for hip surgery planning and dysplasia evaluation." Medical Imaging 2008: Visualization, Image-Guided Procedures, and Modeling. vol. 6918. International Society for Optics and Photonics, 2008. (Year: 2008).*

(Continued)

*Primary Examiner* — Katrina R Fujita
(74) *Attorney, Agent, or Firm* — WCF IP

(57) ABSTRACT

Femoral version impacts the long-term functioning of the femoroacetabular joint. Accurate measurements of version are required for success in total hip arthroplasties and hip reconstructive surgeries. An automated algorithm is provided for identifying the major landmarks of the femur. These landmarks are then used to identify proximal axes and create a statistical shape model of the proximal femur. With six proximal axes selected, and 200 parameters (distances and angles between points) from the shape model measured, the best-fitting linear correlation is found. The difference between true version and version predicted by this model was 0.00°±5.13° with a maximum overestimation and underestimation of 11.80° and 15.35°, respectively. This model and its prediction of femoral version are a substantial improvement over pre-operative 2D or intra-operative visual estimation measures. Acetabular orientation is also determined by an automated algorithm using radii of curvature measurements.

8 Claims, 11 Drawing Sheets
(4 of 11 Drawing Sheet(s) Filed in Color)

(51) Int. Cl.
*G06T 7/00* (2017.01)
*G16H 10/60* (2018.01)

(52) U.S. Cl.
CPC ... *A61B 2034/105* (2016.02); *A61B 2034/108* (2016.02); *G06T 7/0012* (2013.01); *G06T 2207/10081* (2013.01); *G16H 10/60* (2018.01)

(58) Field of Classification Search
CPC ... A61B 2034/108; G06T 7/0012; G06T 7/12; G06T 7/64; G06T 7/73; G06T 2207/10081; G06T 2207/30008; G16H 10/60; G16H 30/20; G16H 30/40; G16H 50/50
See application file for complete search history.

(56) References Cited

U.S. PATENT DOCUMENTS

| | | | | |
|---|---|---|---|---|
| 2012/0143037 | A1* | 6/2012 | Najarian | G06T 7/11 600/407 |
| 2016/0157751 | A1* | 6/2016 | Mahfouz | A61B 6/5211 600/409 |
| 2016/0157936 | A1* | 6/2016 | Netravali | A61B 34/10 606/80 |
| 2016/0253846 | A1* | 9/2016 | Scanlan | A61B 5/055 345/419 |
| 2017/0323443 | A1* | 11/2017 | Dhruwdas | G06T 7/0012 |
| 2019/0133693 | A1* | 5/2019 | Mahfouz | A61B 6/12 |
| 2019/0231434 | A1* | 8/2019 | Lambers | A61B 34/10 |

OTHER PUBLICATIONS

Durgin III et al. "Novel potential marker for native anteversion of the proximal femur." Journal of Orthopaedic Research 35.8 (2016): 1724-1731. (Year: 2016).*

Unlu et al. "Intraoperative estimation of femoral anteversion in cementless total hip arthroplasty using the lesser trochanter." Archives of orthopaedic and trauma surgery 131.9 (2011): 1317-1323. (Year: 2011).*

Worlicek et al. "Lesser trochanter size on plain anteroposterior radiographs correlates with native femoral anteversion." The Journal of arthroplasty 32.9 (2017): 2892-2897. (Year: 2017).*

* cited by examiner

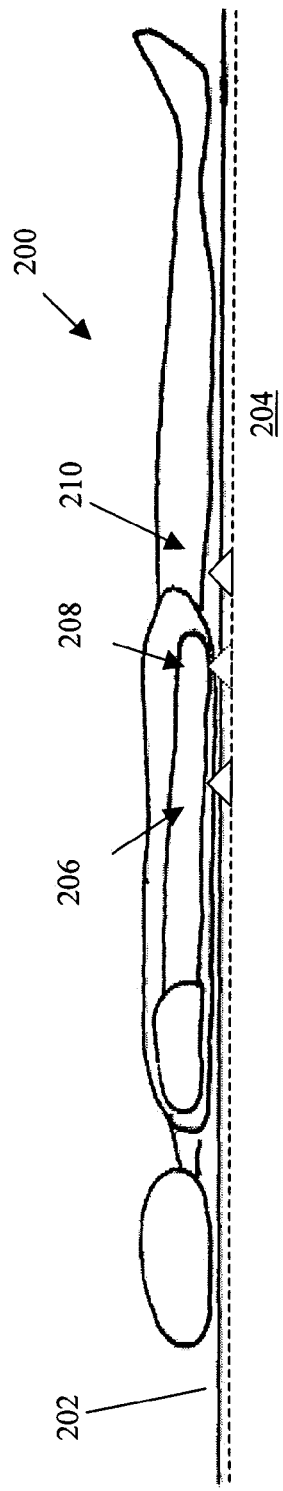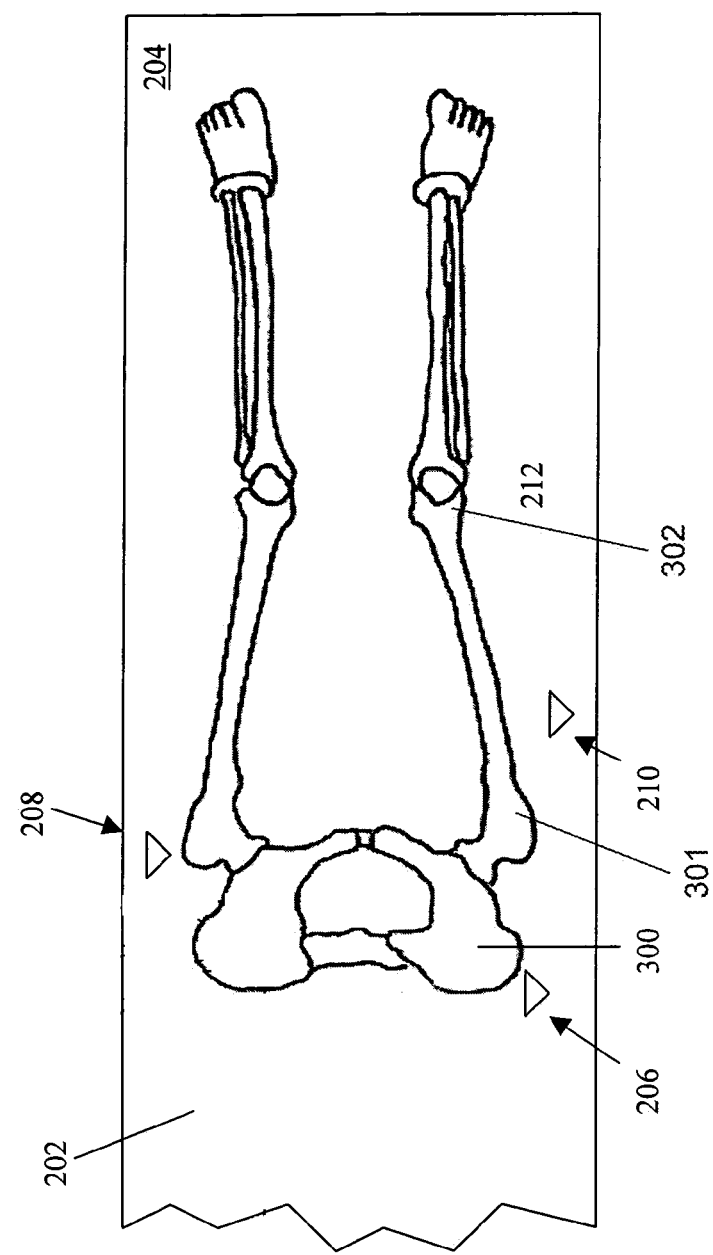
Figure 2
Figure 3

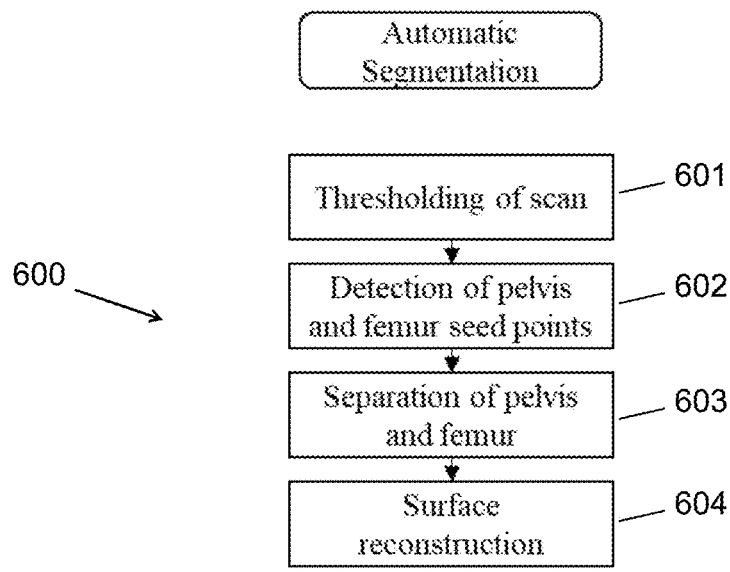
Figure 6
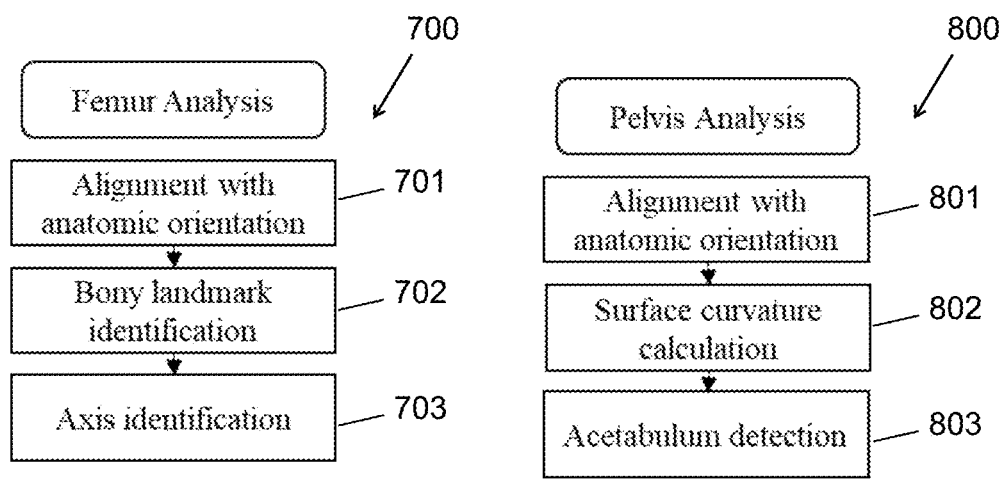
Figure 7
Figure 8

AUTOMATED HIP ANALYSIS METHODS AND DEVICES

CROSS-REFERENCE TO RELATED APPLICATIONS

This application claims the benefit of U.S. Provisional Application No. 62/648,602, filed Mar. 27, 2018, the complete contents of which are herein incorporated by reference.

FIELD OF THE INVENTION

The application relates to computer devices and software offering pre-operative analysis of subject morphology to improve surgical planning and outcomes, and particularly modeling and analysis tools for bones of the hip joint.

BACKGROUND

Proper orientation of the femoral head and neck is required for normal biomechanical function of the hip. Two important relationships for this orientation are femoral inclination and femoral version. Abnormal femoral version is common in patients with labral tears, dysplasia, femoroacetabular impingement, cerebral palsy, and arthritis. It is present in 52% of patients with either symptomatic hip dysplasia or femoroacetabular impingement. A retroverted femur orientation is also associated with less improvement after reconstructive surgery for femoroacetabular impingement.

In total hip arthroplasty, version of the femoral component has a narrow window of acceptability. Excessive anteversion or retroversion leads to impingement between the prosthetic neck and acetabular component causing increased wear and instability. The microscopic debris particles generated in the wear process can induce an inflammatory process which results in bone resorption and aseptic loosening over time. Implant failure due to aseptic loosening has been reported to be responsible for 73.9% of total hip arthroplasty revisions in Sweden from 1979 to 2003. In the US, 378,000 total hip replacements and 105,000 partial hip replacements are performed each year. The incidence of dislocation or instability is 0.3 to 10% after primary total hip replacements and between 6 and 21% after revision total hip replacements. As such, femoral neck version must be accurately measured and corrected for long-term function of the hip joint.

Unfortunately, while acetabular version is approximated by the cross-over sign visible from a 2D radiographic view in the frontal plane, pre-operative measurement of femoral version is not possible with 2D radiography. When viewing axial slices with CT, the orientation of the femoral neck axis changes with respect to the slice level. A 2D view does not accurately capture the 3D nature of version as the 3D femoral neck axis presents differently from both superior and inferior aspects.

CT or MR imaging would permit more accurate measurements by creating 3D models of the femur, however manually selecting the 3D femoral neck axis is challenging. This situation is further hampered in that the scan is limited to the region around the joint to limit radiation exposure, and does not include the distal femur for representation of the posterior condylar line. As such, alternatives to the posterior condylar line must be identified for accurate estimation of version. New axes have been proposed, such as the posterior lesser trochanter line, and the midcortical line. However, correlation of such alternate measures to true anteversion is low.

Intraoperatively, measurement of femoral version is often made but has been found to have a large degree of inaccuracy. Current intraoperative measurements are variable and are different depending on the type of surgical approach used. The posterior, lateral, and tableless anterior approaches involve the surgeon estimating the angle between the neck axis and the long axis of the tibia (which is parallel to distal femoral epicondylar plane with the knee flexed 90 degrees). For the anterior approach performed on a special table, the surgeon estimates version between the femoral neck axis and the long axis of the foot, estimated by the first ray of the foot.

Accurate version estimation is difficult even for experienced surgeons: studies have demonstrated the difference between true and predicted version from surgical estimation to be 1.5±11.3°, and the maximum over- and underestimation to be 30° and 25°, respectively. In addition, component version in total hip arthroplasty has a very limited capacity for adjustment after implantation, due to the bony constraints of the proximal medullary canal.

SUMMARY

An aspect of some embodiments is an automated system for 3-dimensional analysis and measurement of the femur.

An aspect of some embodiments is the use of an automated system to estimate femoral version using surgically-available proximal femur landmarks but eliminating sources of human discrepancy and error while also allowing for multifactor modeling of femoral inclination and femoral version.

An aspect of some embodiments is the use of only proximal femur features (excluding distal features like the condyles). As the femoral condyles cannot be seen intraoperatively and are not generally included in cross sectional imaging data of the hip, a technique that utilized only proximal femoral landmarks to assess femoral version is superior.

Some embodiments of the invention provide a computer algorithm and supporting program that is capable of automatically analyzing the morphology of the femur and pelvis, providing necessary measurements for clinical diagnostic and reconstructive purposes of the hip. This process is entirely automated, capable of accepting 3D models of the femur and pelvis or a CT scan of the hip as inputs.

Some embodiments of the program have three main parts—creating 3D models of femur and pelvis directly from DICOM CT images, morphologic analysis of the femur, and morphologic analysis of the pelvis. It circumvents problems faced by other analytical techniques in two main ways—it eliminates errors associated with manual measurements and is able to make accurate estimates of surgical measures when the scan field is limited to only the proximal femur and pelvis.

In some embodiments, an exemplary program may be used as a diagnostic and pre-operative planning tool, as it accurately provides information required for hip reconstructive surgery. It may also be implemented into CT scanners able to provide measurements given only a scan of the hip region. Some embodiments may include performing a surgery, surgical step, or surgical method using measures or other determinations discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 illustrates a side view of a subject in a supine position.

FIG. 3 shows an overhead skeletal view of a lower portion of the subject of FIG. 2 in a supine position.

FIG. 6 shows a subprocess for exemplary automatic segmentation.

FIG. 7 shows a subprocess for exemplary femur analysis.

FIG. 8 shows a subprocess for exemplary pelvis analysis.

DETAILED DESCRIPTION

Figure 1:
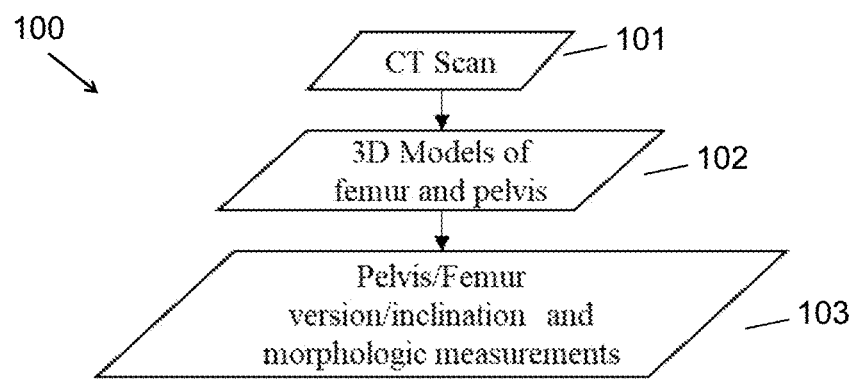
FIG. 1 is a method for automated analysis of a subject's medical morphology.

FIG. 1 is a method 100 for automated analysis of a subject's medical morphology. In some embodiments the method 100 is fully automated. A computer (or computers, depending on the embodiment) receive medical imaging data 101, create one or more 3D models 102 of one or more of a femur and pelvis from the medical imaging data, and automatically determine one or more morphologic characteristics 103 such as version and inclination using the 3D model(s) 102.

Two important relationships for proper orientation of the femoral head and neck are femoral inclination and femoral version. Femoral inclination, or angle of inclination, is the angle formed between the femoral neck axis and the axis of the femoral shaft, in the frontal plane and averages between 120 to 125 degrees in the normal adult hip. Femoral version is the anterior deviation of the femoral neck axis from the posterior condylar line and averages 14.0±6.0° in the normal population, indicating that the femoral head is normally anteverted or oriented anteriorly.

FIG. 2 illustrates a side view of a patient 200 in a supine position on an upper surface 202 of a platform 204. In the embodiment shown in FIG. 2, the platform may be the bed or table of an imaging device such as a CT scanner or MRI machine. When the patient 200 is oriented in this position, the patient's pelvic bone (shown as 300 in FIG. 3) becomes oriented with respect to the upper surface 202 of a platform 204. In the embodiment shown in FIG. 2, arrows 206, 208, 210 generally indicate a scan field. Arrows 206 and 210 may identify the superior and inferior limits of the scan fields.

In some embodiments, method 100 accepts what may be a relatively limited scope of medical imaging data 101 yet generates reliable and accurate measurements 103. The medical imaging data may be of a subject's pelvis 300 and landmarks and features of only the proximal femur 301. In other words, the medical imaging data may not describe the distal femur 302. FIG. 3 shows an overhead skeletal view of a lower portion of the subject of FIG. 2 in a supine position. Here again arrows 206 and 210 are visible and, if treated as the scan field boundaries in an embodiment, exclude the distal femur 302 from imaging, in particular the condyles. The medical imaging data may be CT or MRI images characterized by a scan field limited to the pelvis and only the proximal femur of a subject. Medical imaging data 101 may be DICOM data and/or data configured for compliancy with some other standard known now or adopted in the future. In other embodiments, the table plane 212 may be different than illustrated, or may be another angle other than substantially horizontal, depending on the configuration of the upper surface 202 of the platform 204.

Using for example a computer-aided surgical navigation system, a user such as a surgeon can use the information 103 from method 100 in a surgical procedure, such as installing, mounting, or orienting an acetabular cup or component with respect to a patient's pelvic bone. It should be appreciated that the subject or patient, though depicted as a human, may alternatively be an animal in some instances, e.g., bovine (e.g., cattle), equidae (e.g., horses), canines, felines, or other animals.

Figure 4:
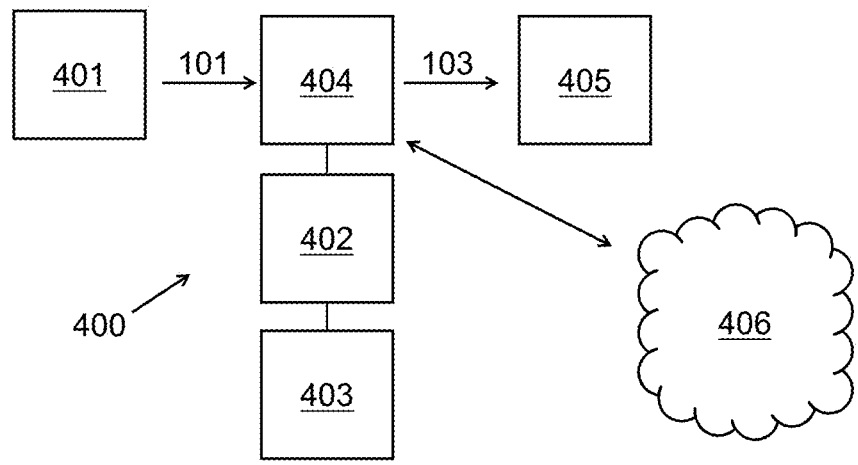
FIG. 4 shows a schematic of a computer or computer system configured to perform the method of FIG. 1.

FIG. 4 shows a schematic of a computer 400 or computer system configured to perform method 100 of FIG. 1. The computer may comprise one or more processors 402, memory 403 (volatile and non-volatile), input/output hardware 404, and other supporting elements generally known in the computing arts (e.g., a power source) omitted for clarity. Though single blocks are used in FIG. 4 to illustrate discrete elements, the blocks serve to illustrate embodiments which may have single instances of an element or multiple instances of an element. For example, many exemplary computers 400 may have a plurality of processors all of which are characterized together as 402.

Medical data 101 is received by computer 400, e.g. by a wired or wireless connection. The data may be transferred over a network connection 406. The determined morphologic characteristics 103 are subsequently output to an output device 405 which may be but is not limited to a display, a computer-aided surgical navigation system, a downstream digital data storage device, or some other apparatus. The computer 400 may itself be or be part of a medical imaging apparatus like a CT scanner or MRI machine.

Figure 5:
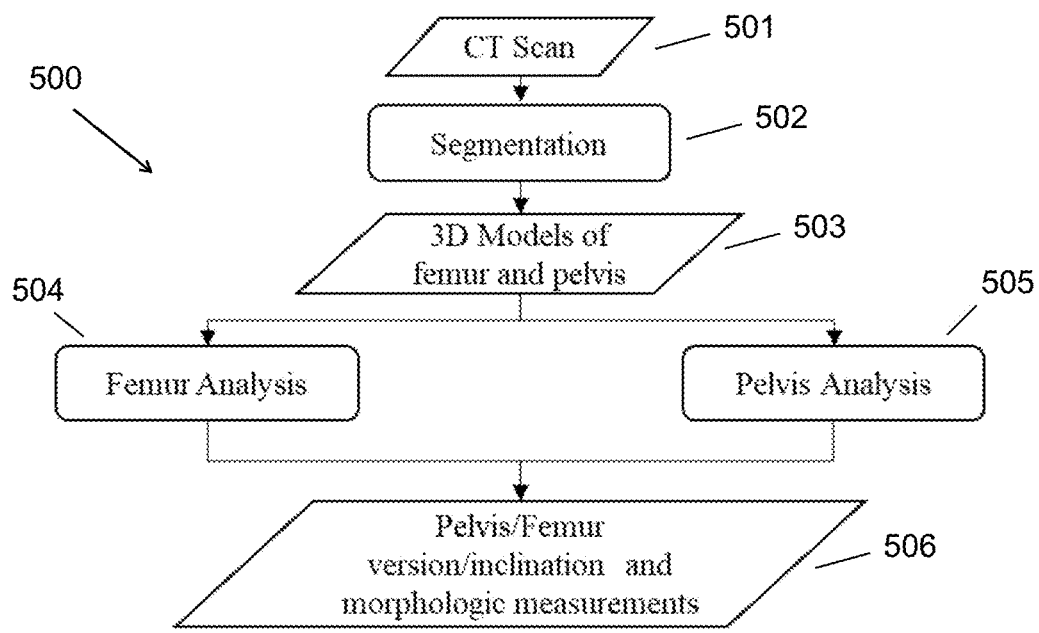
FIG. 5 depicts a method that highlights exemplary stages of processing for achieving automated analysis of a subject's medical morphology from medical imaging data.

FIG. 5 depicts a method 500 that highlights exemplary stages of processing for achieving automated analysis of a subject's medical morphology from medical imaging data. Three steps or blocks are appreciated from the figure. Segmentation 502 is performed on medical imaging data to generate 3D model(s) 503 of the femur and pelvis. The models 503 are then processed according to a femur analysis 504 and a pelvis analysis 505. From these respective analyses, pelvis/femur version/inclination are measured along with other morphologic measurements 506.

FIG. 6 shows a subprocess 600 for exemplary automatic segmentation. The automatic segmentation comprises thresholding the medical imaging data (block 601), detecting pelvis and femur seed points (block 602), separating pelvis and femur (block 603), and reconstructing surfaces (block 604). Automatic segmentation is the process by which a 3D surface is obtained from CT data. "Segmentation" may encompass a variety of techniques for performing this task. In some exemplary embodiments, thresholding 601 is a first step at segmentation. It is a process of marking any CT data above a specific intensity level and is typically used as an initial isolation of bone within the scan. Detection of pelvis and femur seed points 602 addresses a common problem in automatic segmentation of the hip, namely that the femur and pelvis may appear connected within the scan. To guarantee their separation, detection is first made of locations that are known with 100% certainty are on either the femur or pelvis. For separation of pelvis and femur 603, the two bones are separated by first detecting points known to be in the space between them. This information is then used to approximate the shape of the femoral head. When the femoral head is known, it can be easily detached from the pelvis. Surface reconstruction 604 is the process of converting the selections of the femur and pelvis within the CT data to a surface model. It involves detecting and fixing any errors within the surface.

FIG. 7 shows a subprocess 700 for exemplary femur analysis. The femur analysis comprises alignment with anatomic orientation (block 701), bony landmark identification (block 702), and axis identification (block 703).

Block 701 ensures the 3D femur model(s) that serves as an input are consistent with a predetermined reference orientation. For example, as the orientation of the femur may differ among CT scans, 3D models built from the scans may have discrepancies in initial orientation. Block 701 brings the femur into a reproducible orientation via principal component analysis. This orientation is comparable to the ISB recommended femur coordinate system, though it differs in that the resulting sagittal plane is susceptible to changes due to femoral version.

At block 702, the major landmarks of the femur identified may include one or more (e.g., all of) the following: femoral head, femoral neck, greater and lesser trochanters, linea aspera, posterior condylar line, and femoral shaft. Example 1 provides an exemplary specific set of procedures which may be employed for identifying these respective landmarks.

Femoral head identification may be achieved, for example, by iterative fitting of spheres to a series of points, beginning with a seed point, until a sphere contains an entirety of the femoral head.

Femoral neck may be identified as a line fit to centroids of ellipses fit to a plurality of cross-sections of the femoral neck region. Cross-section diameters may be used to determine boundary conditions. When the major axis of a cross section exceeds a threshold percentage of a predetermined minimum identified diameter (e.g., 130%), the ellipse fitting is terminated. A determination may be made whether overlap is detected between the identified femoral neck and femoral head, and the latter made to exclude the part of the model identified with the former.

The femoral shaft may be identified by iterative fitting circles in the transverse plane, starting at e.g. the midsection of the femur. The shaft search may be terminated proximally upon finding a current section to exceed a predetermined threshold of the midsection radius (e.g., 120%) and distally upon finding a current section to exceed a second predetermined threshold of midsection radius (e.g., 160%).

Curvature may be assessed for regions above the identified shaft, and the region of greatest curvature identified as the lesser trochanter.

Some bony landmarks may be identified by process of elimination. Provided head, neck, shaft and less trochanter are first identified, the vertices and faces of these landmarks (in the 3D model) may be removed from consideration and the remainder of the model (unassigned region superior and lateral to the lesser trochanter) identified as the greater trochanter.

Posterior condylar line may be defined as a line connection the posterior-most points of the medial and lateral condyles.

Figure 11:
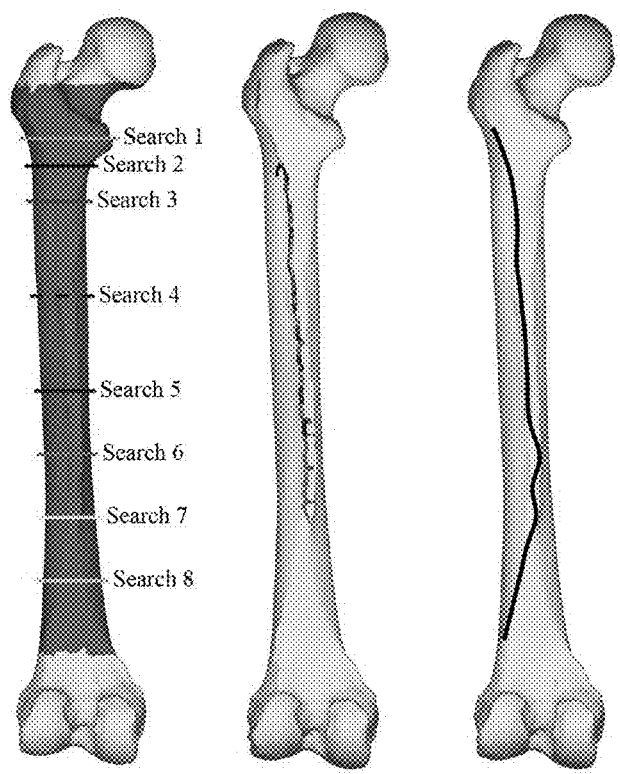
FIG. 11 illustrates linea aspera identification including: (left side) starting points of linea aspera search, resulting curves isolated to region in red; (middle) combined results of the 8 different searches, each search examined transverse slices created iteratively more proximal and distal from the start location, identifying regions of high curvature near the previous slice; (right side) resulting lateral lip of linea aspera defined as the median of the 8 previous curves. Only the proximal portions of the linea aspera were used for calculations in some embodiments.

Linea aspera may be identified by taking a series of transverse slices of the region identified as the shaft, such as depicted in FIG. 11. The curvatures of slices may be measured and a point for the linea aspera set on the posterior surface of the femur where the curvature is highest. Slices may be iteratively made until the curvature at all points of a slice fall below a predetermined threshold. It should be appreciated that although FIG. 11 shows a 3D model of a whole femur, a distal portion (e.g., condyles) may be absent from the 3D model(s) of some embodiments owing to the medical imaging data (e.g., CT data) not including data for this region.

At block 703, axes are identified. In particular, in some embodiments, some or all of the axes identified are proximal axes. The axes identifies may include one or more (e.g. all) of the following: lesser trochanter axis (LTA), intertrochanteric axis (ITA), maximum diameter axis (MDA), maximum diameter greater trochanter axis (MDAGT), posterior calcar axis (PCA), and greater trochanter calcar axis (GTC). Exemplary definitions for automatic identification of each these axes is provided in Example 1 below.

Figure 14:
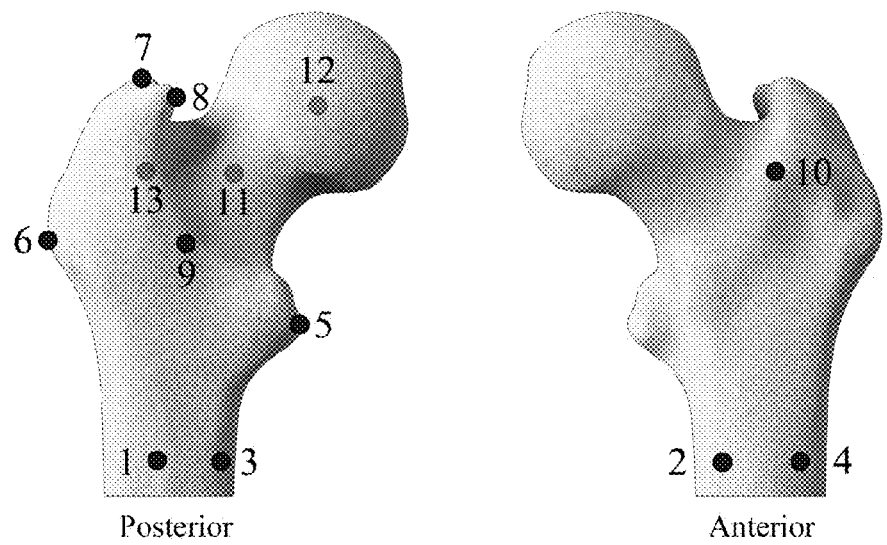
FIG. 14 shows thirteen points used in statistical shape model of proximal femur.
Figure 15:
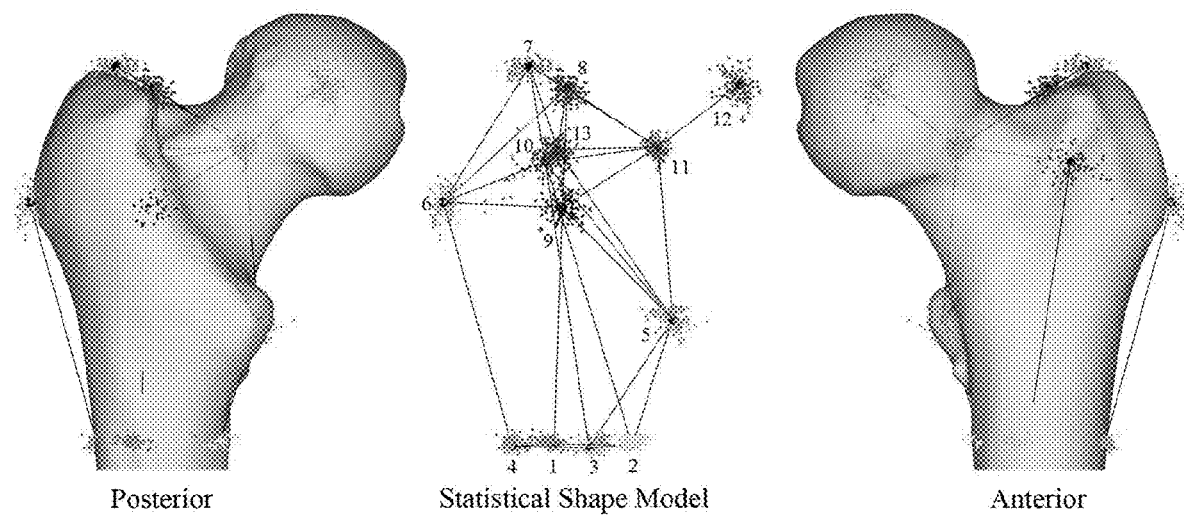
FIG. 15 is a point distribution model showing locations of each point in the statistical shape model across all 144 femora (from Example 1) after shape is normalized through generalized Procrustes analysis. A representative surface model is shown superimposed over the mean shape model in the anterior and posterior views. Variation in the automatically identified linea aspera due to the presence of the third trochanter can be seen in orange. Points 11, 12, and 13 are deep to the outer surface in the anterior and posterior views shown (muted shading).

A statistical shape model (SSM) may be created using a plurality of consistently-identifiable points. Consistently-identifiable means across multiple 3D models produced for multiple different subjects, the same points are identifiable automatically within a predetermined margin of discrepancy or error. The SSM is not strictly necessary for characterization of the femur and pelvis in all embodiments. It may be used for a subset of femurs in which the entire bone is not visible. Thirteen exemplary consistently-identifiable points are described in Example 1 below and illustrated in FIG. 14. FIG. 15 illustrates the general consistency of identifying the same thirteen points across a sample group of 144 femora each from a different subject. The model depicted in the posterior and anterior views of FIG. 15 are illustrative for a single subject's femur model.

FIG. 8 shows a subprocess 800 for exemplary pelvis analysis. The pelvis analysis comprises alignment with anatomic orientation (block 801), surface curvature calculation (block 802), and acetabulum detection (803). Block 801 ensures the 3D femur model(s) that serves as an input are consistent with a predetermined reference orientation. For example, as the orientation of the pelvis may differ among CT scans, 3D models built from the scans may have discrepancies in initial orientation. Example 2 below provides a detailed illustrative procedure for a pelvis analysis consistent with FIG. 8.

Figure 9:
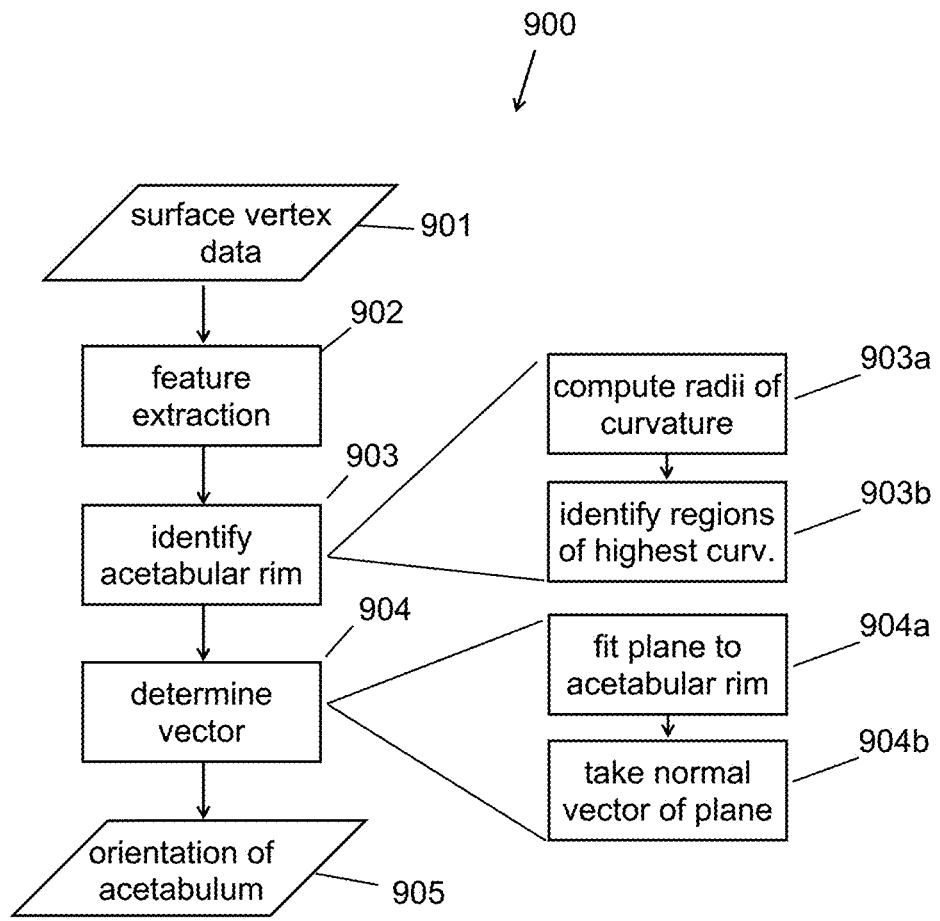
FIG. 9 shows an exemplary method of assessing acetabular orientation.
Figure 17A:
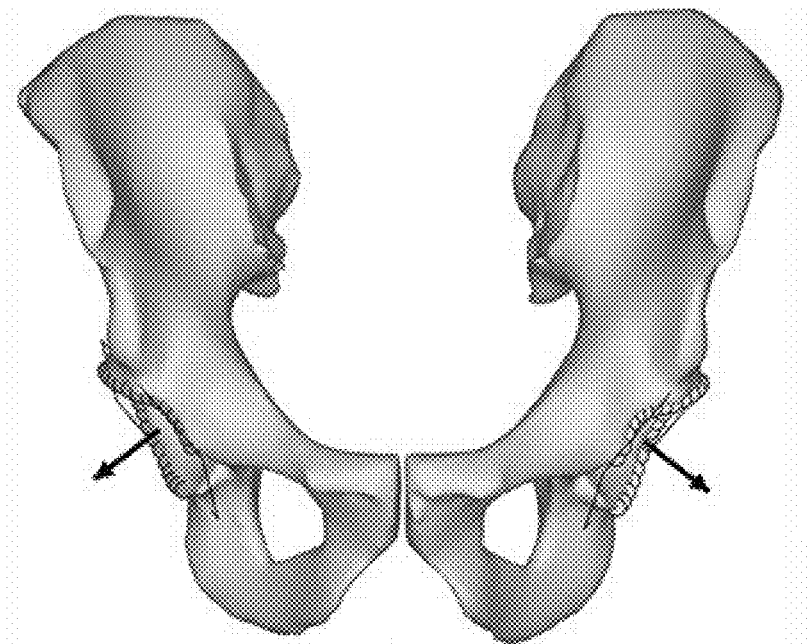
FIG. 17A shows automated detection of acetabular orientation with normal vector (black arrow) designated.

FIG. 9 shows a method 900 of assessing acetabular orientation at a more specific level of detail from FIG. 8. Files containing surface vertex data 901 for a subject specific pelvis are an exemplary input to the method 900. The surface vertex data 901 may be from or permit creation of a 3D model such as depicted by FIG. 17A. However, method 900 or similar Feature extraction 902 may be performed on this input data to identify, for example, the anterior pelvis plane (APP). This may be achieved by first locating a plurality of points (minimum three to define a plane), such as the left and right anterior superior iliac spines and the centroid of the left and right pubic tubercles. From the extracted features, the acetabular rim is identified at block 903. The high curvature of the acetabular rim makes radii measures a suitable means for this identification. Radii of curvature may be computed across the entire pelvis (903a), and the measures may be compared against one another and/or a predetermined threshold to identify regions of highest curvature (903b). Exemplary illustration for this is provided in FIG. 17B. Blue dots are assessed points and pink dots are identified as tracing the acetabular rim. Next, at 904 a vector is determined from the acetabular rim. The points corresponding with highest curvature trace a curve, and a plane may be fit to this curve (904a). A normal vector may then be taken from the plane (904b). This normal vector may be output as the orientation of the acetabulum 905.

Figure 10:
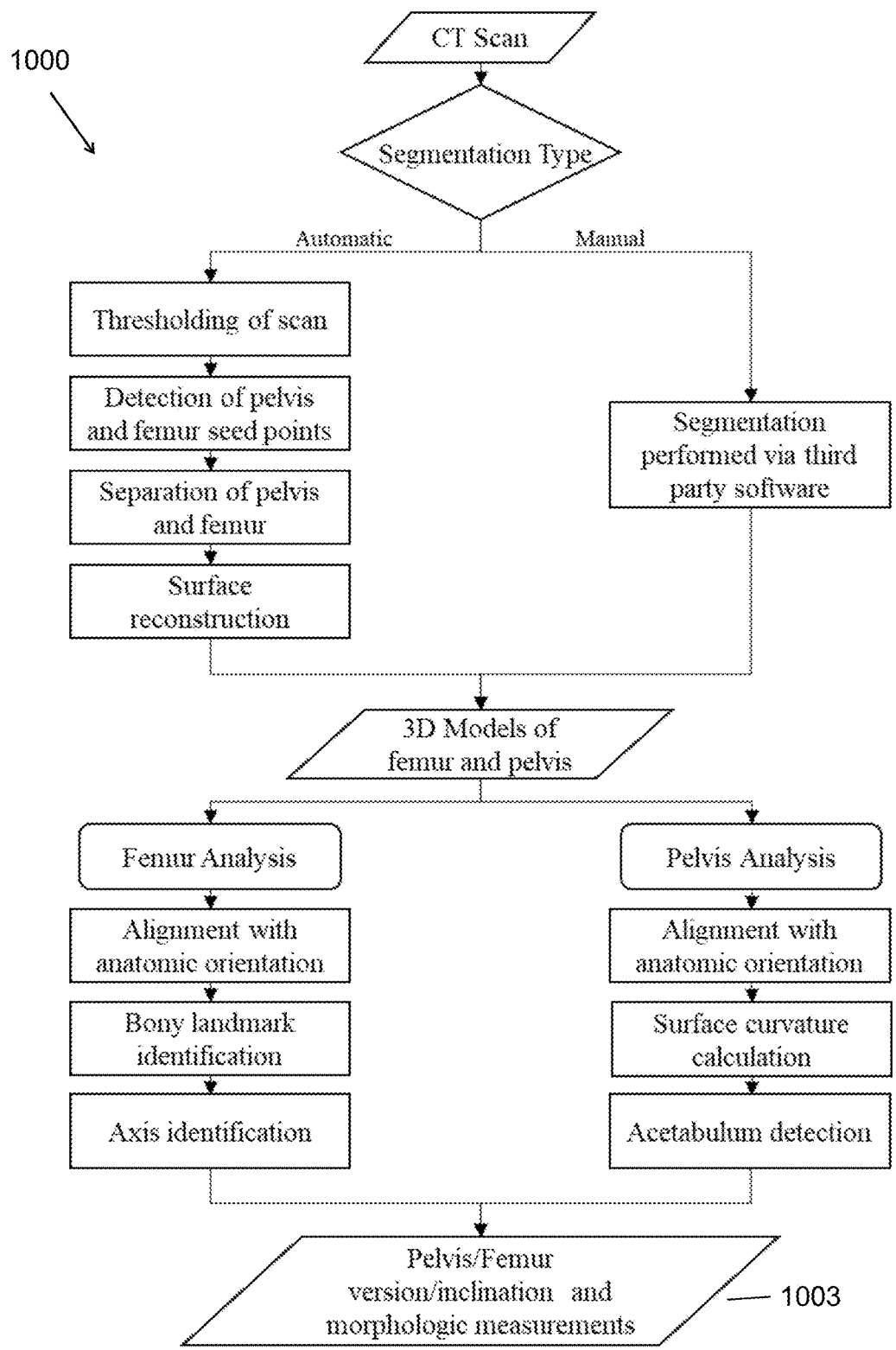
FIG. 10 shows a method combining processes and subprocesses of preceding figures.

FIG. 10 shows a method 1000 that puts together the exemplary processes and sub-processes of preceding figures. Note that segmentation may proceed by an automatic route or manual route.

In a number of exemplary embodiments automated segmentation is preferred and leverages some of the key advantages of the instant invention, including elimination of variation from human error and discretion.

A culmination of the generation of 3D models and conducting femur analysis and pelvis analysis is the subsequent automated determination of version, inclination, and morphological measurements (103 in FIG. 1, 1003 in FIG. 10). From the bony landmarks and axes determined in process 700 (FIG. 7), hundreds of parameters may be produced as candidates for measuring true version. Example 1 presents an exemplary statistical method of refining the candidates to a reduced list of, e.g., 45 parameters (from an original 200 parameters in the example). Linear combinations of the parameters may be made to determine specific measures. A 14-point linear combination example is presented in Example 1. Output measurements may include one or more of femoral version, inclination, alpha angle, presence of osteoarthritis, for example.

Further findings, outputs, and implications of the method 1000 are discussed below within the examples.

The present invention may be a system, a method, and/or a computer program product. The computer program product may include a computer readable storage medium (or media) having computer readable program instructions thereon for causing a processor to carry out aspects of the present invention.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

The following are non-limiting examples illustrative of some aspects of some embodiments of the invention.

Example 1—Femur Analysis

Methods

This Example illustrates a feature recognition algorithm to automatically identify multiple femoral landmarks from 3D rendered femora. Six potential axes for calculating version, all based on landmarks visible during hip surgery, were automatically identified. Further, the algorithm was used to create a statistical shape model of the proximal femur from a series of landmark points. Distances and angles contained between sets of points in the statistical shape model as well as the angles between the six potential axes and the femoral neck axis were considered in establishing a mathematical relationship for predicting true version from these measures.

Feature Recognition: 3D models of 144 full length femurs (72 patients, mean age 57±13.8 yrs; 46:26 male:female) were created from CT scans segmented in Mimics (Materialise, Leuven Belgium). Automatic feature extraction was performed in Matlab (MathWorks, Natick Mass.) on the resulting stereolithography (.stl) files containing the vertices and faces for each bone. As the orientation of the femur may differ between CT scans, the process of feature recognition began with bringing each femur into a reproducible orientation via principal component analysis. This orientation is comparable to the ISB recommended femur coordinate system, though it differs in that the resulting sagittal plane is susceptible to changes due to femoral version. From here the following major landmarks of the femur were identified: femoral head, femoral neck, greater and lesser trochanters, linea aspera, posterior condylar line, and femoral shaft.

The femoral head search began with a seed point located at the most medial and proximal point of the femur. Spheres were iteratively fit to the neighboring points until a sphere containing the entire femoral head was found. The sphere fit returns more points of the head with each iteration. In an exemplary embodiment, it was found that this process returns the femoral head (or enough of the femoral head to allow for the analysis to proceed) consistently after three iterations. The femoral neck axis was identified as the line fit to the centroids of ellipses fit to cross sections of the femoral neck. The ellipse fitting ceased in the medial and lateral directions when the major axis of the current cross section exceeded 130% of the minimum identified diameter. This value was chosen to stop the search before it incorporated the femoral head, and correlates well to visual estimations of the neck. Any overlap between the identified head and neck is removed from the head, and the sphere defining the head refined.

The femoral shaft was identified by iteratively fitting circles in the transverse plane, starting at the midsection of femur. The shaft search was cut off proximally when the radius of the current section exceeded 120% of the midsection radius, and was cut off distally when the radius of the current section exceeded 160% of the midsection radius. This defined the shaft as the region distal to the lesser trochanter and proximal to the adductor tubercle. The lesser trochanter was identified as the region of greatest curvature in the medial femur above the identified shaft. With the vertices and faces identified as belonging to the head, neck, shaft, and lesser trochanter removed, the greater trochanter was identified as the unassigned region superior and lateral to the lesser trochanter.

Figure 12:
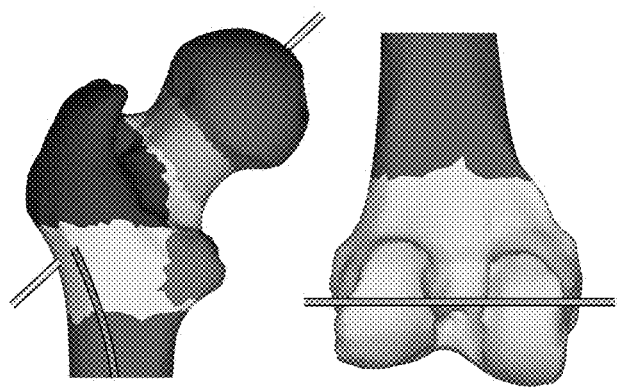
FIG. 12 shows color coded regions identified by a feature recognition algorithm such as in the method in FIG. 7.

The posterior condylar line was defined as the line connecting the posterior-most points of the medial and lateral condyles, from which true version was measured between this line and the neck axis. The linea aspera was obtained by analyzing the curvature of a transverse slice of the identified shaft region (FIG. 11). Then the curvature of adjacent transverse slices was analyzed, keeping the region of high curvature closest to those previously identified. This process continued until no region of high curvature near the previously selected point was found. This entire search process was repeated 8 times, initiated at different points along the long axis of the femur, with the linea aspera calculated as the median of the 8 resulting curves. The results of the feature recognition algorithm may be seen in FIG. 12: femoral head (red), femoral neck (cyan), greater trochanter (dark blue), lesser trochanter (magenta), femoral shaft (dark green), linea aspera (orange), posterior condylar line (light green), femoral neck axis (yellow), unassigned regions (light blue).

Figure 13:
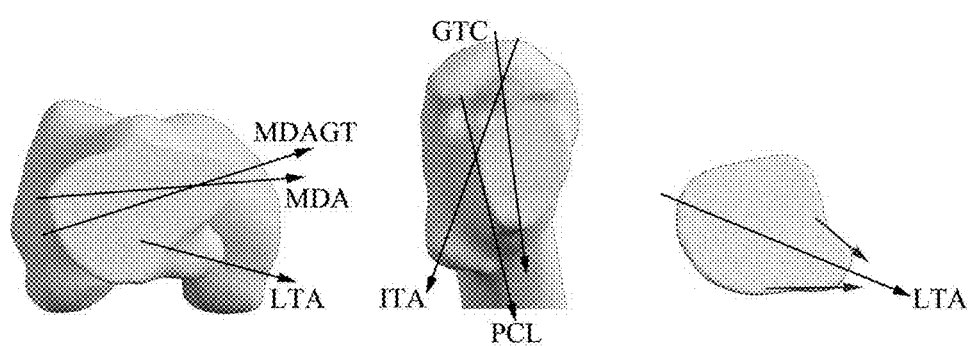
FIG. 13 shows six proximal axes which may be used in version prediction: (left side) MDAGT, MDA, and LTA visible in the transverse plane; (middle) GTC, PCL, and ITA visible in the plane of the neck resection; (right side) 2-vector sum used to calculate LTA, performed in a transverse slice of the femur at the level of the lesser trochanter.

Six Proximal Axes: Following the production of an intra-operatively-accessible predictor of femoral version, six proximal axes were assessed (FIG. 13): lesser trochanter axis (LTA), intertrochanteric axis (ITA), maximum diameter axis (MDA), maximum diameter greater trochanter axis (MDAGT), posterior calcar axis (PCA), and greater trochanter calcar axis (GTC). The maximum diameter axis has been defined previously as the axis connecting the two most distant points in a section of the femoral shaft in the transverse plane two centimeters above the lesser trochanter. The maximum diameter greater trochanter axis differs from the MDA axis in that the lateral-most point used is the centroid of the greater trochanter projected onto the cut plane. The greater trochanter calcar axis was defined as the axis connecting the most medial point at the base of the cut plane to the midpoint of the greater trochanter. The midpoint was identified as the area between the anterior and posterior surfaces of the greater trochanter, evaluated 2 cm below the superior-most point of the greater trochanter (some embodiments may use a threshold other than 2 cm). The posterior calcar line was defined as the line fit to the linear portion of the calcar region after the femoral neck has been resected. The intertrochanteric axis was defined as the line connecting the midpoint of the greater trochanter (used in the GTC axis definition) to the apex of the lesser trochanter. The lesser trochanter axis was defined as the sum of two unit vectors fit to the anterior and posterior surfaces of the lesser trochanter (FIG. 13).

Statistical Shape Model: In addition to the six proximal axes, a statistical shape model was created of the proximal femur using 13 consistently-identifiable points (FIG. 14): (points 1-4) 4 points 90° offset from one another 2 cm below the lesser trochanter, with the first point centered on the lateral lip of the linea aspera; (point 5) apex of the lesser trochanter; (point 6) lateral-most edge of the greater trochanter, directly superior to the iliotibial tract, defined mathematically as the region on the lateral greater trochanter with the highest curvature; (point 7) superior-most aspect of gluteus minimus insertion, defined as the most superior point on the greater trochanter; (point 8) proximal peak of the greater trochanter; (point 9) posterior-most aspect of quadrate tubercle, defined as the posterior-most point of the greater trochanter; (point 10) anterior-most aspect of intertrochanteric line, defined as the anterior-most point of the greater trochanter; (point 11) femoral neck centroid; (point 12) femoral head center; (point 13) trochanteric fossa, defined as the region of greatest curvature between the identified femoral neck and the peak of the greater trochanter.

Some of the points of this model were defined as regions of greatest curvature or the further extent along a specific anatomic axis. These points were normalized to a mean shape model created through generalized Procrustes analysis (FIG. 15). Procrustes analysis attempts to match two shapes to one another via translation, rotation, and scaling. Generalized Procrustes analysis continues this concept to create a mean shape to which other shapes can be matched. FIG. 15 is a point distribution model showing locations of each point in the statistical shape model across all 144 femora of this Example after shape is normalized through generalized Procrustes analysis. A representative surface model is shown superimposed over the mean shape model in the anterior and posterior views. Variation in the automatically identified linea aspera due to the presence of the third trochanter can be seen in orange. Points 11, 12, and 13 are deep to the outer surface in the anterior and posterior views shown (muted shading).

From the 13 points and six proximal femur axes, 200 different measurements were extracted: the 3D angles between sets of 3 points, the 2D angles between sets of 3 points, the distances between each point, the distance between each point and the respective point in the mean shape model, the 3D angle between each of the six proximal axes and the femoral neck axis, and the 2D angle between each of the six proximal axes and the femoral neck axis. For reference, the 3D angle refers to the magnitude of the angle between two vectors in space, while the 2D angle refers to the projection of this angle onto the transverse plane.

Statistical Analysis: Each of the 200 measured parameters measured was considered individually as a predictor for true version. The six 2D proximal angles were selected initially as they are visible intra-operatively. For each pair of these angles (a total 15 pairs), a linear regression model was computed with true version as the outcome and the two angles and their interaction as predictors; then the fitted value from this model was entered into a Bland Altman analysis and the limit of agreement (LOA) recorded. In addition, a linear model that included all six angles as main effects was considered as a predictor. Subsequently, linear models of the others parameters were considered. Any parameter with MSE (mean squared error)>7° was eliminated, as these parameters gave no discernable relationship between predicted and true version. Linear models were then created from permutations of the remaining parameters using 50-fold cross-validation with the goal to achieve a deviation of less than 11°, the variation found in the intra-operative measurement approach. This linear model was then applied to 20 additional femurs not used in the creation of the statistical shape model.

Results

To characterize the hips included in this example, inclination, alpha angle, and presence of osteoarthritis were measured in addition to version. The median version angle, often referred to as femoral torsion, was 15.5° (range 20.1-52.3°, IQR 9.1-21.9°). Literature indicates IQR version ranges from 7.4 to 20.4°. The median femoral neck angle, also referred to as inclination, was 129.4° (range 100.8-147.9°, IQR 125.4-133.3°. IQR inclination ranges from 117.9 to 125.6°. This version and inclination data indicate the subjects included in this example reflect measures comparable with the population at large as presented in a study of over 1,000 individuals. The median alpha angle was 44.4 (range 35.3-79.5°, IQR 41.1-47.7°. Normal alpha angles are considered to be less than 55°. The measures of alpha angle in this example population indicate that 9.8% of the subjects were at risk for cam-type femoroacetabular impingement. The joints were evaluated by an orthopaedic surgeon for hip arthritis according to the Kellgren-Lawrence (KL) scoring system which ranges from 0 (none) to 4 (severe). Of the 164 hips, 1 had a score of 4, 3 had a score of 3, 5 had a score of 2, 25 had a score of 1, and 128 had a score of 0. The remaining two hips (same subject) could not be graded due to lower CT resolution limiting clarity of the joint space.

The LOA for the original six individual proximal 2D angles ranged from 19.1 to 16.2°, and for pairs of these angles from 18.7 to 14.9°; for the predictor formed from all six proximal 2D angles the LOA was 15.5°. The minimum was achieved by the MDAGT and GTC 2D angles together with their interaction. As these predictions did not yield the desired prediction accuracy, all 200 of the original parameters were considered as potential surrogates. Only 45 of these resulted in an MSE<7°, and linear combinations of parameters were considered. The best was a 14-point model using the following parameters (in which ∠x-y-z refers to the angle between points x, y, and z with point y as the vertex): 1) 2D angle between MDAGT and the neck axis; 2) 2D angle ∠8-7-11; 3) 3D angle ∠6-8-11; 4) 2D angle between ITA and neck axis; 5) 3D angle ∠8-7-10; 6) 3D angle ∠10-7-11; 7) 3D angle ∠8-7-11; 8) distance between points 2 and 3; 9) distance between points 8 and 9; 10) 3D angle ∠8-9-11; 11) 2D angle ∠5-10-7; 12) 2D angle ∠7-8-11; 13) 2D angle ∠5-10-6; 14) 2D angle ∠9-11-8. The estimated version predicted by this model was compared to true version using Bland-Altman analysis. FIG. 16B is a Bland-Altman plot of true vs. predicted version in Example 1.

Figure 16A:
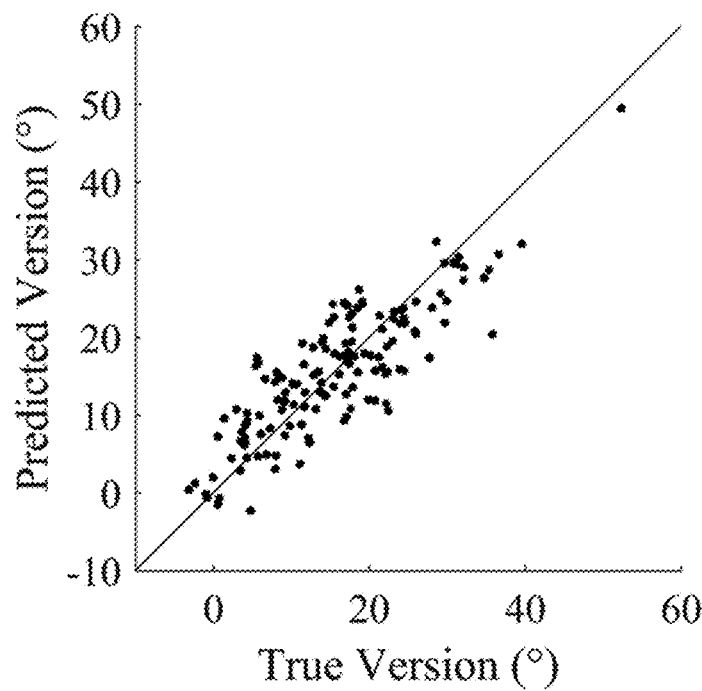
FIG. 16A is a scatterplot of true version vs. version predicted by 14-parameter linear model in Example 1.
Figure 16B:
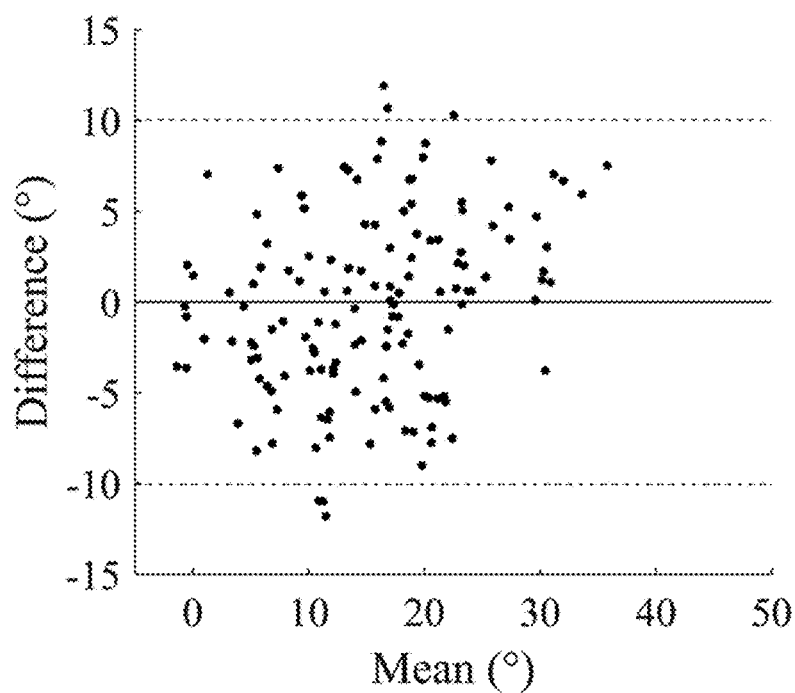
FIG. 16B is a Bland-Altman plot of true vs. predicted version in Example 1.

The version predicted by the 14-parameter linear model (15.68±8.25°) had an average identical to true version (15.68±9.72°) (FIG. 16A). The difference between the predictions had a mean of 0.00° and standard deviation of 5.13°. The mean absolute deviation of true and predicted version were 7.68° and 6.43°, respectively. Of the 144 observations, 95% fell within ±10.05° difference from true version. The maximum overestimation and underestimation were 11.80° and 15.35°, respectively. The root-mean-square error of the linear model was 5.76°, with an R-squared value of 0.65. The model was then used to predict version on 20 femurs not used in the creation of the statistical shape model. The difference between true and predicted version for these femurs was consistent with those found previously (mean 0.1°, SD 4.65°.The difference between true and predicted version between male and female subjects was −0.34±4.62° and 0.61±5.92°, respectively. No significant difference between predictions for the two was found.

Discussion

The 14-parameter linear model developed in this example demonstrates a marked improvement in prediction of true femoral version over 2D approaches as well as intraoperative measurements. When the distal condyles were scanned for axial views in prior studies, 2D presentations of the neck axis resulted in version measures that differed from true version by an average of 8.6° with a maximum over- and underestimation of 33 and 14°. In general, two-dimensional approaches suffer from insufficient reflection of the 3D orientation of the femoral neck in a 2D image. The linear model also shows a significant improvement over intraoperative surgical estimation, which has a difference between true and predicted version from surgical estimation as 1.5±11.3°, and the maximum over- and underestimation of 30° and 25°, respectively. With intraoperative estimation, the femoral condyles are palpated to approximate the posterior condylar line. As the femoral neck axis is visible intraoperatively, the angle between these two axes is then approximated by the surgeon.

In initially searching for a surrogate measure for true version, each parameter was first considered individually as an alternate predictor of true version by simple linear regression. As none were individually sufficiently reflective of true version, linear models with multiple parameters were considered which resulted in the 14-parameter model. Other improvements to the model were considered. Artificial neural networks may improve the prediction over the simple linear model. Given the large number of parameters, the 14-parameter model may not be single optimum solution, but one of multiple acceptable solutions. While this example validated the selection using MSE as a means to eliminate less promising parameters, an analysis of every possible permutation of the 200 parameters was infeasible for purposes of the example. As the precision of intraoperative positioning with computer navigation is 4.8° and the average difference between 2D and 3D methods is 8.6 degrees, further model improvements may not result in better clinical outcomes.

In exemplary embodiments, multiple features (e.g., six determined axes instead of a single axis, for example) are included simultaneously to average out the variance in any individual feature. Logically, version estimation via multiple predictors is not feasible intraoperatively, and must be performed algorithmically. The linear model herein addresses this issue by incorporating all of the distinct bony landmarks of the proximal femur. The statistical shape model attempts to minimize the differences between patients by normalizing size and orientation, leaving only differences caused by individual feature variation. The predictions made by this model are thus based on the aggregate of all anatomic variation possible in the proximal femur. With the proposed linear model, much more accurate predictions of femoral version are made. This may be used to assist in the surgical planning process for total hip arthroplasties and reconstructive surgeries. Its use intraoperatively may be via a reference axis generated by the version angle provided preoperatively from the linear model to the visible neck axis.

As our linear model predicts femoral version without landmarks from the shaft or distal femur, one may question the origin of femoral version. The angle between the femoral neck and posterior condylar line is influenced by neck orientation, torsion of the shaft, as well as condylar twist. Thus, two identical proximal femora could exist with substantially different version angles. As this does not seem to be the case in the femurs analyzed in example 1, there may be contributions from the shaft and distal femur present within the proximal femur itself. Of course, contributions to femoral version from shaft torsion and condylar twist may have added to the variability in the resulting measures of this example.

There is a degree of error affecting the choice of parameters for the linear model. The linea aspera search was hampered in patients where the third trochanter (one category of bony growths on the posterior surface of the proximal femur superior to the lesser trochanter) was present. Similar error is present in other parameters due to bone spurs and osteophytes. This degree of variation led to the rejection of the angles and distances associated with these points. Some embodiments may include in the feature detection algorithm a step of identifying random bone spurs and other irregularities. Additionally, each of our landmark identifications made use of 3D definitions, as it is expected that they will be more accurately representative of the anatomy than the standard radiograph-based 2D definitions. Morphologic measures of this example population indicate that the subjects well represented characteristics of the population at large which is important for applicability of the linear model. The hips were largely non-arthritic indicating further study is warranted on severely diseased joints.

This work indicates that femoral version may be accurately determined preoperatively with or without the distal femur. Furthermore, this process has been automated for analysis of the femur without human intervention. The relative orientation between femur and acetabular, or the combined version as the sum of the femoral and acetabular versions, is influential in normal hip function. While an understanding of femoral version is required for reconstructive surgery and accurate placement of the femoral stem in a total hip arthroplasty, knowledge of combined version is also useful surgically. There exists only a small range of acceptable values for the combined version: between 30° to 60° were reported to minimize the risk for impingement and maximize functional range of motion. The risk for dislocation has also been reported to be 6.9 times higher if the combined anteversion does not lie within 40° and 60°. As such, accurate measurements of both femoral and acetabular version are crucial for the long term success of total hip arthroplasties, femoroacetabular impingement surgery, and maintenance of normal joint function. The automated calculation of acetabular inclination and version may be as two algorithms or a combined algorithm for preoperative planning of hip surgery.

Example 2—Pelvis Analysis

Figure 17B:
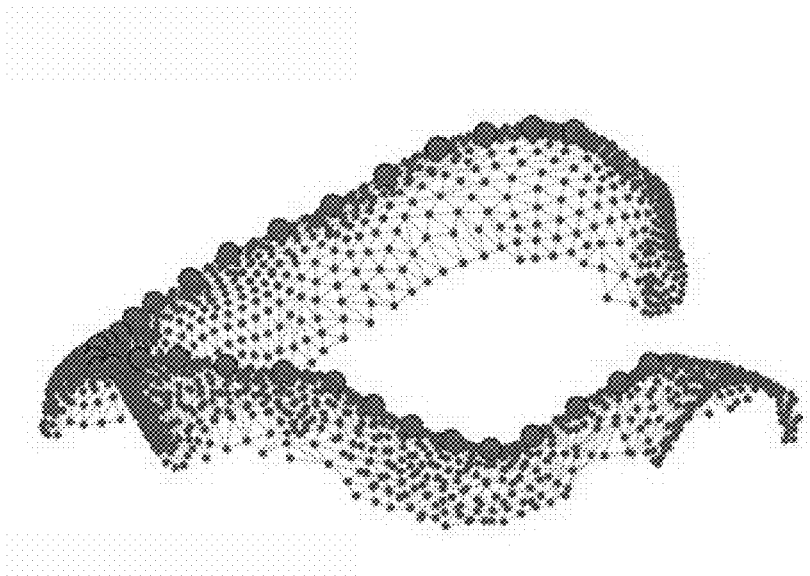
FIG. 17B shows automatic acetabular rim selection.

Methods 3D models of 200 pelvises (200 patients, mean age 41±14.5 yrs; 82:118 male:female) were obtained from CT scans segmented in Mimics (Materialse, Leuven Belgium). Feature extraction was performed in Matlab (MathWorks, Natick Mass.) on the resulting stereolithography (.stl) files containing surface and vertex data for each pelvis. The algorithm began by detecting the anterior pelvis plane (APP) defined by three points: the left and right anterior superior iliac spines and the centroid of the left and right pubic tubercles. This was accomplished by creating a convex hull of the pelvis which always contained a plane connecting the three of these points, allowing consistent identification. The program then detected an approximate location of the acetabula by measuring anterior deviation at each point of the anterior pelvis. The selection of the acetabula was further refined by computing radii of curvature across the entire pelvis, knowing the acetabular rim to be a region of high curvature. A graph was then created using the vertices and edges of the identified rim and a curve traced along the regions of highest curvature, resulting in a single curve spanning the entire acetabular rim. A plane was fit to the curve, with the normal vector representing the orientation of the acetabulum (FIGS. 17A and 17B).

Results

The difference between version and inclination measures calculated by the proposed automated algorithm and the established semi-automated algorithm had a mean of −0.17° with a standard deviation of 1.20. 95% of measurements made by the automatic algorithm lay between −0.17±2.36° of validated results.

Discussion

The proposed automatic algorithm yielded nearly identical results to prior methods which were partly manual. Minor variation occurred in a prior solution in which manual point selection was required to initialize a semi-automated algorithm. This form of variance was corrected in the proposed automated algorithm, as the rim selection was based on pre-defined rules instead of user discretion. This algorithm allows for accurate and rapid measurement of acetabular orientation.

While exemplary embodiments of the present invention have been disclosed herein, one skilled in the art will recognize that various changes and modifications may be made without departing from the scope of the invention as defined by the following claims.

We claim:

1. A computer-implemented method for automated analysis of a subject's medical morphology, comprising
receiving medical imaging data;
creating one or more three-dimensional (3D) models of one or more of a femur and pelvis from the medical imaging data, wherein the creating step comprises automatic segmentation comprising
thresholding the medical imaging data;
detecting pelvis and femur seed points; and
separating pelvis and femur by detecting points known to be in the space between them and approximating the shape of the femoral head; and
reconstructing surfaces based on the separating step;
automatically determining one or more morphologic characteristics using the one or more 3D models; and
analyzing the femur of the one or more 3D models, wherein the analyzing step comprises the steps of
aligning with anatomic orientation;
identifying bony landmarks; and
identifying one or more proximal axes, wherein the one or more proximal axes are selected from the group consisting of lesser trochanter axis (LTA), intertrochanteric axis (ITA), maximum diameter axis (MDA), maximum diameter greater trochanter axis (MDAGT), posterior calcar axis (PCL), and greater trochanter calcar axis (GTC),
wherein the one or more proximal axes comprise each of lesser trochanter axis (LTA), intertrochanteric axis (ITA), maximum diameter axis (MDA), maximum diameter greater trochanter axis (MDAGT), posterior calcar axis (PCL), and greater trochanter calcar axis (GTC).

2. The computer-implemented method of claim 1, wherein the medical imaging data are of a subject's pelvis and only the proximal femur.

3. The computer-implemented method of claim 2, wherein the medical imaging data are computerized tomography (CT) or magnetic resonance imaging (MRI) images with scan field limited to the pelvis and only the proximal femur of a subject.

4. The computer-implemented method of claim 3, wherein the medical imaging data are Digital Imaging and Communications in Medicine (DICOM) data.

5. The computer-implemented method of claim 1, further comprising analyzing a pelvis of the one or more 3D models, the analysis comprising
aligning with anatomic orientation,
calculating surface curvatures, and
detecting acetabulum from the curvatures.

6. The computer-implemented method of claim 1, wherein the determining step comprises determining one or more of femoral version, inclination, and alpha angle.

7. The computer-implemented method of claim 6, further comprising using a determined femoral version, inclination, or alpha angle in a medical procedure.

8. The computer-implemented method of claim 1, wherein the one or more proximal axes are algorithmically averaged to reduce variation.

\* \* \* \* \*